United States Patent [19]

Thorp et al.

[11] Patent Number: 5,171,853

[45] Date of Patent: Dec. 15, 1992

[54] PROCESS OF CLEAVING NUCLEIC ACIDS WITH OXORUTHENIUM(IV) COMPLEXES

[75] Inventors: H. Holden Thorp, Cary; Neena Grover, Raleigh, both of N.C.

[73] Assignee: North Carolina State University, Raleigh, N.C.

[21] Appl. No.: 740,048

[22] Filed: Aug. 5, 1991

[51] Int. Cl.$^5$ .............................................. C07H 21/00
[52] U.S. Cl. ........................................ 536/27; 536/28; 536/29; 546/2
[58] Field of Search ............................. 536/27, 28, 29

[56] References Cited

U.S. PATENT DOCUMENTS

| | | | |
|---|---|---|---|
| 3,793,355 | 2/1974 | Wilkinson | 556/21 |
| 4,235,868 | 11/1980 | Cleare et al. | 424/3 |
| 4,699,978 | 10/1987 | Barton | 536/27 |
| 4,980,473 | 12/1990 | Barton | 546/10 |

FOREIGN PATENT DOCUMENTS 956241 of 1964 United Kingdom .
956242 of 1964 United Kingdom .

OTHER PUBLICATIONS

Grover et al., *Chem. Abstr.*, 115(11), p. 344, Abstr. No. 108,747f (1991).
McHatton et al., *Chem. Abstr.*, 101, p. 415, Abstr. No. 237,152t (1984).
B. Moyer et al., *J. Am. Chem. Soc.* 102, No. 7, 2310–2312 (1980).
M. Thompson and T. Meyer, *J. Am. Chem. Soc.* 104, 4106–4115 (1982).
M. Thompson and T. Meyer, *J. Am. Chem. Soc.* 104, 5070–5076 (1982).
M. Thompson et al., *J. Org. Chem.* 49, 4972–4977 (1984).
A. Dovletoglou et al., *J. Am. Chem. Soc.* 112, 8989–8990 (1990).

Primary Examiner—Johnnie R. Brown
Assistant Examiner—L. Eric Crane
Attorney, Agent, or Firm—Bell, Seltzer, Park & Gibson

[57] ABSTRACT

A method of cleaving nucleic acids comprises contacting a nucleic acid to an oxoruthenium(IV) coordination complex. Examples of coordination compounds useful for carrying out the method include $Ru^{IV}(tpy)(bpy)O^{2+}$, $Ru^{IV}(typ)(phen)O^{2+}$, $Ru^{IV}(typ)(tmen)O^{2+}$, $Ru^{IV}(bpy)_2(py)O^{2+}$, and $Ru^{IV}(phen)_2(py)O^{2+}$.

4 Claims, 3 Drawing Sheets

PROCESS OF CLEAVING NUCLEIC ACIDS WITH OXORUTHENIUM(IV) COMPLEXES

FIELD OF THE INVENTION

This invention relates to the use of oxoruthenium (IV) complexes for cleaving nucleic acids.

BACKGROUND OF THE INVENTION

The oxidative cleavage of DNA by metal complexes is important in drug applications, the development of synthetic restriction enzymes, and studies of tertiary DNA structure. (S. Hecht, *Acc. Chem. Res.* 1986, 19, 83; S. Lippard, *Acc. Chem. Res.* 1978, 11, 211; J. Barton, *Science* 1986, 233, 727; P. Dervan, *Science* 1986, 232, 464; A. Burkhoff et al., *Nature* 1988, 331, 455; T. Tullius and B. Dombrosk., *Science* 1985, 230, 679).

Tris(polypyridyl) complexes of Rh(III) and Co(III) cleave DNA efficiently upon UV ($<350$ nm) photolysis. Derivatization of one or more of the chelating ligands has shown that this cleavage can be made both stereo- and shape-selective (A. Pyle et al., *J. Am. Chem. Soc.* 1990, 112, 9432; A. pyle et al., *J. Am. Chem. Soc.* 1989, 212, 4520; J. Barton and A. Raphael, *J. Am. Chem. Soc.* 1984, 106, 2466). In these systems, it is primarily the photochemistry of the polypyridyl ligands that is responsible for the oxidative cleavage.

The complexes cis-$Ru^{IV}(bpy)_2(py)O^{2+}$ and $Ru^{IV}(tpy)(bpy)O^{2+}$ (bpy=2,2'-bipyridine, tpy=2,2',2''-terpyridine) oxidize organic hydrocarbons and alcohols via hydride transfer to form $Ru^{II}OH^+$ and a carbocation (T. Meyer, *J. Electrochem. Soc.* 1984, 131, 221C; M. Thompson and T. Meyer, *J. Am. Chem. Soc.* 1982, 104, 4106), but have not been suggested for use in cleaving nucleic acids.

J. Barton, U.S. Pat. No. 4,699,978, discloses the use of ruthenium (II) complexes for labeling RNA (see col. 1 line 67 to col. 2 line 8) and the use of Cobalt (III) complexes (see col. 1 lines 55–60) for selectively nicking DNA.

SUMMARY OF THE INVENTION

We have now found that coordination complexes of oxoruthenium(IV) are useful for cleaving nucleic acids without the need for UV photolysis. Thus, the method of the present invention comprises contacting a nucleic acid to an oxoruthenium(IV) coordination complex of the formula L-$Ru^{IV}O^{2+}$, with the coordination complex provided in an amount effective to cleave the nucleic acid. L is an inert nitrogen-containing ligand or an inert nitrogen-containing ligand set, and contains five nitrogen atoms bonded to $Ru^{IV}$ by coordination bonds.

The foregoing and other aspects of the present invention are discussed in detail in the specification and drawings set forth below.

BRIEF DESCRIPTION OF THE DRAWINGS

FIG. 3 1% Agarose ethidium bromide gels showing the electrophoresis of solutions containing 60 μM pSport1 DNA with (A) no ruthenium and with 20 μM [$Ru^{II}$(tpy)(bpy)OH$_2$(ClO$_4$)$_2$ electrolyzed at 0.8 V for (B) 15 min., (C) 30 min., and (D) 1.5 h. (E) 60 μM pSport1 with no ruthenium. (F) 60 μM pSport1 that has been electrolyzed at 0.8 V in the absence of metal complex for 2 h. (G) 60 μM pSport1 incubated at 25° C. with 0.2 mM [$Ru^{II}$(tpy)(bpy)OH$_2$(ClO$_4$)$_2$ for 1 h. (H) 60 μM pSport1 incubated with 0.2 mM [$Ru^{IV}$(tpy)(bpy)O](ClO$_4$)$_2$ for 1 h. Molecular weight markers are from DRIgest III (λDNA-Hind III/φX174-Hae III digest) purchased from Pharmacia.

DETAILED DESCRIPTION OF THE INVENTION

Figure 1A:
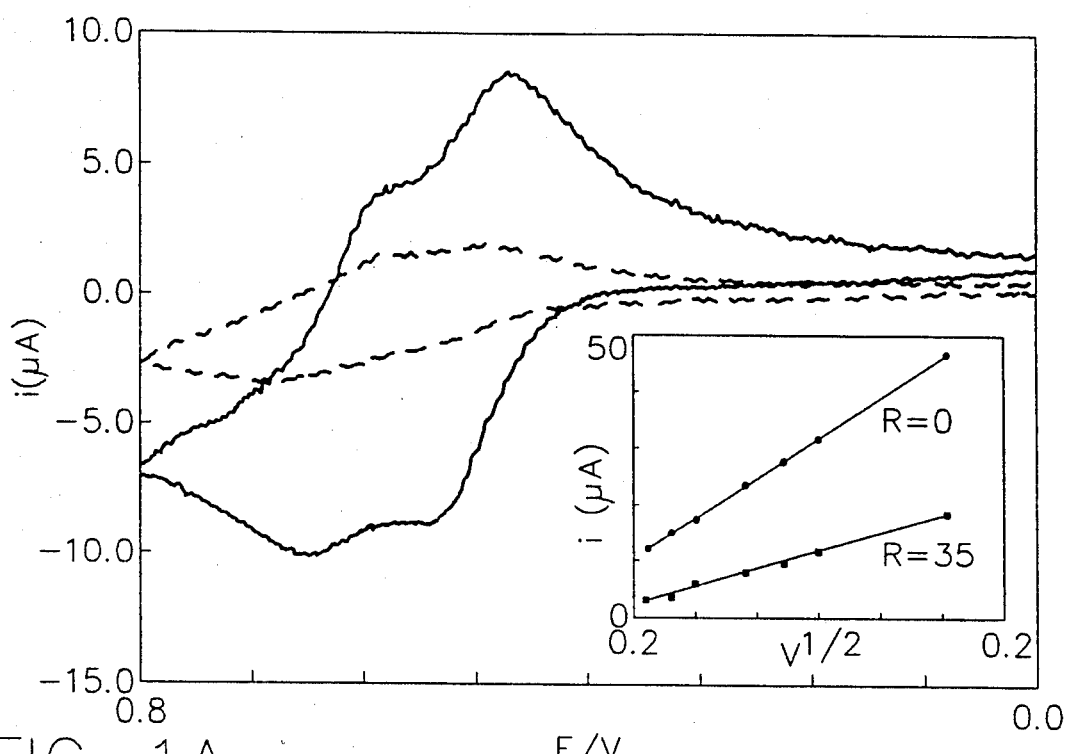
FIG. 1 shows the following: (A) Cyclic voltammograms of 0.2 mM [$Ru^{II}(tpy)(bpy)OH_2$]($ClO_4$)$_2$ in 0.05 M phosphate buffer, pH 7 with (dashed line) and without (solid line) calf thymus DNA (7 mM-nucleotide phosphate). Inset: plot of $i_{pa}$(Ru(III/II)) vs. $v^{\frac{1}{2}}$ in buffer (R=0) and with DNA (R=35). (B) Enlarged cyclic voltammogram in the presence of DNA from FIG. 1A. Inset: plot of $\Delta i_{pa}$ vs. $v^{\frac{1}{2}}$ for the Ru(III/II) and Ru(IV/III) couples. $\Delta i_{pa}=i_{pa}$(buffer)$-i_{pa}$(DNA). Working electrode: tin-doped indium oxide. Reference electrode: Ag/AgCl (1.0 M KCl). Counter electrode: Pt wire. Scan rate: 25 mV/s.
Figure 1B:
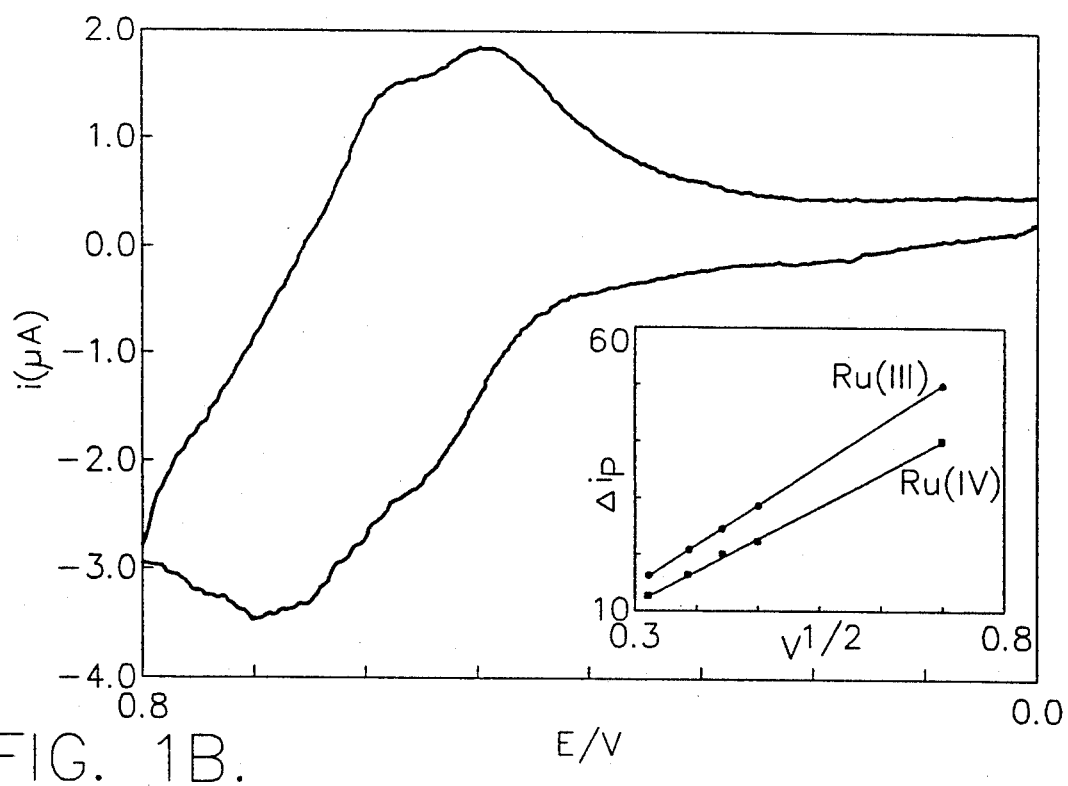

Nucleic acids which may be cleaved by the present invention include both DNA and RNA, with cleavage being caused by oxidation of the sugar moiety of the nucleic acid. The nucleic acid may be single stranded, double stranded, or triple stranded, with cleavage of multiple stranded DNA typically being by single-strand scission.

As noted above, L is an inert nitrogen-containing ligand or an inert nitrogen-containing ligand set, and contains five nitrogen atoms. The coordination complex as a whole has an octahedral orientation, as illustrated by Formula (I) below. The five nitrogen atoms may be carried by five separate organic compounds, or may all be carried by a single organic compound which serves as a pentadentate ligand. In general, nitrogen atoms which participate in a coordination bond with the ruthenium:v should not be covalently bonded to hydrogen in a compound which serves as a ligand or member of a ligand set. When two or more nitrogens are contained in a compound used as a ligand herein, the nitrogens may be positioned in the compound so that all participate in forming coordination bonds with the $Ru^{IV}$. Of course, the compound may contain additional nitrogen atoms which do not participate in forming coordination bonds with the $Ru^{IV}$. The nitrogen-containing compounds may, for example, be a polypyridyl ligand or a polypyridyl ligand set (these terms including the substituted derivatives thereof, as discussed in detail below).

Examples of nitrogen-containing compounds which can be used as ligands or members of ligand sets in the coordination complexes disclosed herein (and the corresponding abbreviations for these compounds employed herein) include: pyridine ( or "py"); 2,2'-bipyridine (or "bpy"); 2,2',2''-terpyridine (or "tpy"); 1,10-phenanthroline (or "phen"); and N,N'-tetramethylenediamine (or "tmen").

Substituted derivatives of the nitrogen-containing compounds disclosed herein are also useful as ligands or members of ligand sets in the present invention. The term "substituted derivative" refers to a compound obtained by replacing one or more hydrogen atoms in the foregoing nitrogen-containing compounds with one or more other moieties having the characteristic that the oxoruthenium (IV) coordination complex containing the resulting compounds binds to a nucleic acid. Such other moieties include, but are not limited to, methyl, ethyl, hydroxy, nitro, amino, dimethylamino, acetyl, and fused ring systems (e.g., phen is a substituted derivative of bpy).

Illustrative substituted derivatives of the foregoing include, but are not limited to, 4-aminopyridine, 4-dimethylpyridine, 4-acetylpyridine, 4-nitropyridine, 4,4'-diamino-2,2'-bipyridine, 5,5'-diamino-2,2'-bipyridine, 6,6'-diamino-2,2'-bipyridine, 4,4'-diethylenediamine-2,2'-bipyridine, 5,5'-diethylenediamine-2,2'-bipyridine, 6,6'-diethylenediamine-2,2'-bipyridine, 4,4'-dihydroxyl-2,2'-bipyridine, 5,5'-dihydroxyl-2,2'-bipyridine, 6,6'-dihydroxyl-2,2'-bipyridine, 4,4',4''-triamino-2,2',2''-terpyridine, 4,4',4''-triethylenediamine-2,2',2''-terpyridine, 4,4',4''-trihydroxy-2,2',2''-terpyridine, 4,4',4''-trinitro-2,2',2''-terpyridine, 4,4',4''-triphenyl-2,2',2''-terpyridine, 4,7-diamino-1,10-phenanthroline, 3,8-diamino-1,10-phenanthroline, 4,7-diethylenediamine-1,10-phenanthroline, 4,7-diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline, 3,8-diphenyl-1,10-phenanthroline, 4,7-dispermine-1,10-phenanthroline, 3,8-disperamine-1,10-phenanthroline, and dipyrido[3,2-a:2',3'-c]phenazine (or "dppz").

Compounds illustrative of the oxoruthenium(IV) coordination complexes disclosed herein include the following:

$Ru^{IV}(tpy)(bpy)O^{2+}$;
$Ru^{IV}(tpy)(phen)O^{2+}$;
$Ru^{IV}(tpy)(tmen)O^{2+}$;
$Ru^{IV}(bpy)_2(py)O^{2+}$;
$Ru^{IV}(phen)_2(py)O^{2+}$; and
$Ru^{IV}(tpy)(tmen-AO)O^{2+}$.

Unless otherwise specified, complexes referred to herein are racemic mixtures of enantiomers.

The compound $Ru^{IV}(tpy)(bpy)O^{2+}$ is shown in Formula (I) below, illustrating the orthogonal configuration of the oxoruthenium(IV) coordination complexes described herein:

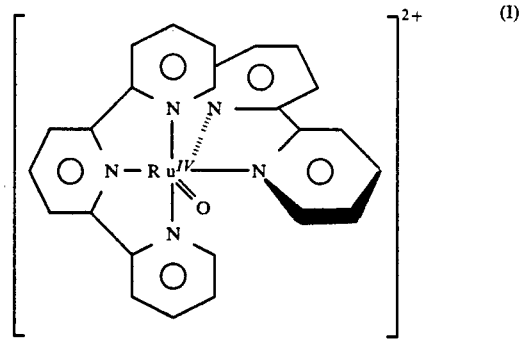

The method of the present invention is useful for cleaving nucleic acids in vitro, such as for diagnostic purposes and for the purpose of determining nucleic acid structure. The method is typically carried out in an aqueous solution at a neutral pH or a pH not disruptive to the nucleic acid to be cleaved (e.g., a pH of 6.5 to 7.5). The biologically active form can be chemically synthesized and added to a reaction solution containing nucleic acids as a stoichiometric oxidant, or the inert form can be added and the active form generated either by chemical oxidation by innocuous, outer-sphere oxidants or electrolysis (e.g., at about 0.8 Volts vs. SSCE or more). The complexes are substitutionally inert and can be generated without UV photolysis. The compounds may be provided in the form of a salt with a suitable couterion, such as a perchlorate, methanesulfonate, ethanesulfonate, or sulfate. The in vitro reaction solution may be a cell-free solution, may contain cell fragments, or may contain whole cells with the nucleic acids to be cleaved contained within those cells.

The method of the present invention may also be used for cleaving nucleic acids in vivo in a human or animal subject in need of such treatment. Thus, a further aspect of the present invention is a pharmaceutical formulation comprising an oxoruthenium(IV) coordination complex as given above in a pharmaceutically acceptable carrier, with the coordination complex being included in an amount effective to cleave nucleic acids. Suitable carriers for parenteral injection include sterile pyrogen-free water and sterile pyrogen-free saline solution; suitable carriers for topical application include topical ointments and creams such as oil-in water creams formulated with polyhydric alcohols (e.g., propylene glycol, mannitol). For use in vivo the coordination complex may be prepared as a pharmaceutically acceptable salt with a counterion which is pharmaceutically acceptable, such as the sulfate, methansulfonate, or ethanesulfonate. Cleavage of nucleic acids may be carried out in vivo for any purpose, typically to inhibit cell growth and/or division in situations of abnormal cell growth or proliferation (e.g., in treating psoriasis and for combatting the growth of a tumor susceptible to the treatment). Thus, the present invention also provides for the use of the oxoruthenium(IV) coordination complexes, including the pharmaceutically acceptable salts thereof, as described above for the preparation of a medicament for cleaving nucleic acids in a subject in need of such treatment, as discussed above. The medicament is prepared in accordance with known techniques, which involve contacting and mixing the medicament with a suitable pharmaceutical carrier, as also discussed above.

The present invention is explained in greater detail in the following non-limiting examples. In the Examples, g means grams, s means seconds, min means minutes, h means hours, mL means milliliters, nm means nanometers, mV means millivolts, mM means millimolar, M means Molar, and temperatures are given in degrees centigrade unless otherwise specified.

EXAMPLE 1

Cyclic Voltammetry of $Ru^{II}(tpy)(bpy)OH_2^{2+}$ $Ru^{IV}(tpy)(bpy)O^{2+}$ and $Ru^{II}(tpy)(bpy)OH_2^{2+}$ were prepared according to K. Takeuchi et al., *Inorg. Chem.* 1984, 23, 1845. Cyclic voltammetry was performed at 0.32 cm² tin-doped indium oxide working electrodes as previously described (H. Thorp et al., *J. Electroanal. Chem.* 1990, 290, 293) using a PAR 273A potentiostat and PAR Model 270 software. Calf thymus DNA was purchased from Sigma and used according to published procedures ($A_{260}/A_{280}=1.8$)(M. Carter and A. Bard, *J. Am. Chem. Soc.* 1987, 109, 7528).

The cyclic voltammogram of $Ru^{II}(tpy)(bpy)OH_2^{2+}$ (FIG. 1A) shows two waves corresponding to the $Ru^{III}(tpy)(bpy)OH^{2+}/Ru^{II}(tpy)(bpy)OH_2^{2+}$ (0.49 V vs. Ag/AgCl) and $Ru^{IV}(tpy)(bpy)O^{2+}/Ru^{III}(tpy)(-$ bpy)OH$^{2+}$ (0.62 V) redox couples. Binding of the metal complex to the nucleic acid causes a decrease in current upon addition of calf thymus DNA (M. Carter et al., *J. Am. Chem. Soc.* 1989, 111, 8901; M. Carter and A. Bard, supra; M. Carter and A. Bard, *Bioconjugate Chem.* 1990, 1, 257. The $i_p$-$v^{\frac{1}{2}}$ plots are linear from 25 mV/s to 500 mV/s, and the y-intercepts are 0 within experimental error (inset). The slope is decreased by 50% in DNA (R=[DNA-phosphate]/[Ru]=35), suggesting a binding constant of $10^3-10^4$ M$^{-1}$, similar to those observed for related complexes. The ratio of $i_p$(Ru(IV))/$i_p$(Ru(III)) is clearly larger in the presence of DNA than in buffer; the current enhancement in the Ru(IV) wave arises from catalytic oxidation of the DNA. Therefore, the loss of current brought about by the addition of DNA is smaller for the Ru(IV/III) couple and linear with $v^{\frac{1}{2}}$ for both couples (see inset).

EXAMPLE 2

Oxidation of calf Thymus DNA by Ru$^{IV}$(tpy)(bpy)O$^{2+}$

Figure 2A:
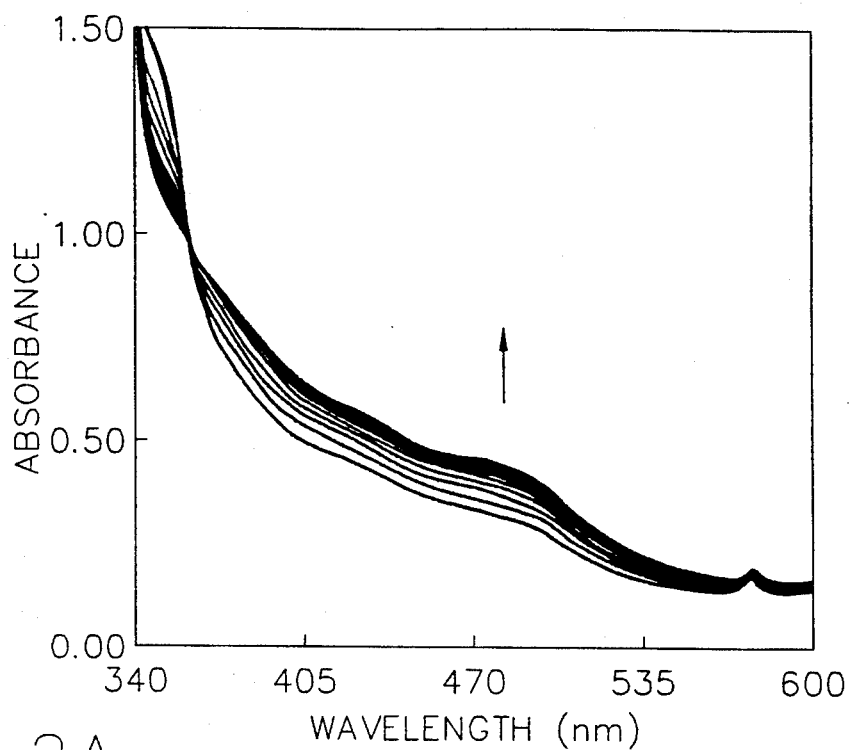
FIG. 2 shows (A) UV-vis spectra taken at 2 min. intervals during the oxidation of calf thymus DNA (0.5 mM-nucleotide phosphate) by [$Ru^{IV}$(tpy)(bpy)O](ClO$_4$)$_2$ (0.5 mM) under N$_2$. (B) UV-vis spectra taken at 5 min. intervals during the oxidation of calf thymus DNA (2 mM) by [$Ru^{IV}$(tpy)(bpy)O](ClO$_4$)$_2$(0.1 mM) under N$_2$.
Figure 2B:
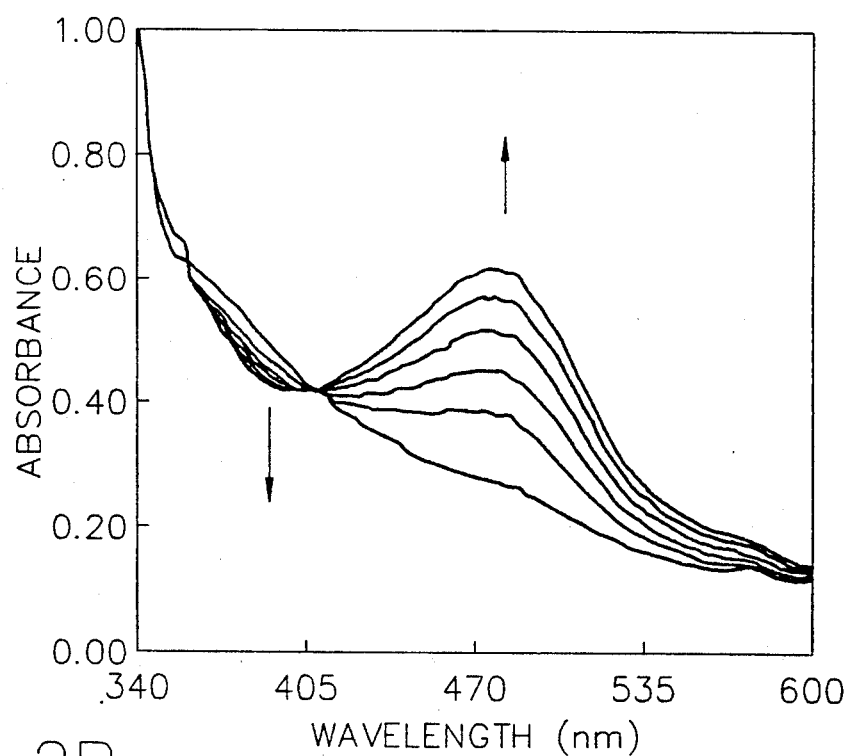

Oxidation of calf thymus DNA can be monitored by optical spectroscopy (R. Binstead and T. Meyer, *J. Am. Chem. Soc.* 1987, 109, 3287: M. Thompson and T. Meyer, *J. Am. Chem. Soc.* 1982, 104, 4106). In this example, UV-vis spectra were acquired on a HP 8452 diode array spectrophotometer. Oxidation by Ru$^{IV}$(tpy)(bpy)O$^{2+}$ dominates the early stage of the reaction, and spectra taken during this stage are characterized by an isosbestic point at 363 nm (FIG. 2A). The later stage is dominated by oxidation of the DNA by Ru$^{III}$(tpy)(bpy)OH$^{2+}$, which is generated by comproportionation of the Ru(IV) and Ru(II) species. Accordingly, a new isosbestic point at 406 nm is observed (FIG. 2B), as is a rapid increase in absorption at 477 nm due to the quantitative formation of the Ru$^{II}$(tpy)(bpy)OH$_2^{2+}$. These observations are identical to those made in the oxidation of iso-propanol (M. Thompson and T. Meyer, *J. Am. Chem. Soc.* 1982, 104, 4106). In solutions containing 0.1 mM calf thymus DNA and 0.1 mM Ru$^{IV}$(tpy)(bpy)O$^{2+}$, the isosbestic behavior at 406 nm is reached in approximately 1 h. Under the conditions shown in FIG. 2B ([DNA]=2 mM, [Ru$^{IV}$(tpy)(bpy)O$^{2+}$]=0.1 mM), the later stage of the reaction is reached before a spectrum can be acquired, i.e. all of the Ru$^{IV}$(tpy)(bpy)O$^{2+}$ is consumed immediately upon mixing with the DNA. The kinetics appear to reflect the extent of binding of the metal complex to the DNA.

EXAMPLE 3

Cleavage of pSport 1 DNA

Figure 3:
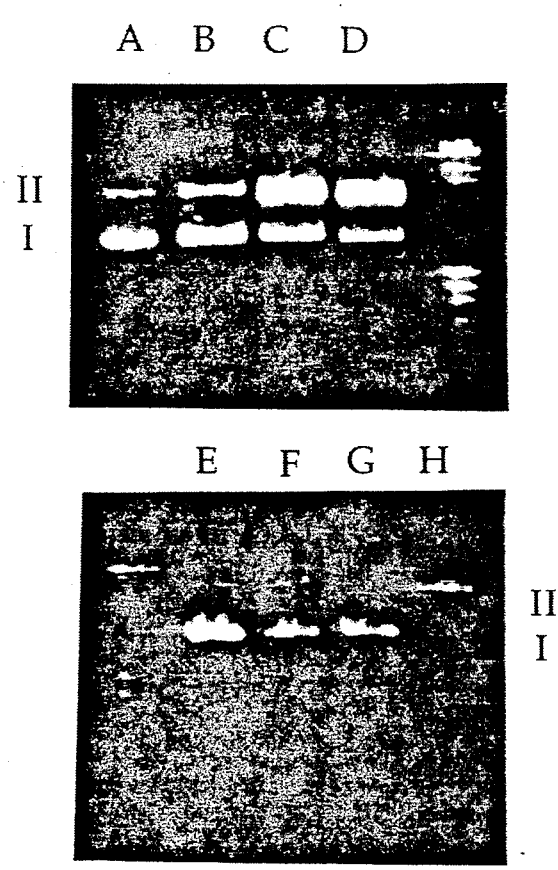

Cleavage of pSport 1 DNA can be observed by monitoring the conversion of supercoiled (form I) to nicked circular (form II) DNA by gel electrophoresis (FIG. 3). Solutions were electrolyzed in the same cell used for cyclic voltammetry above and stirred by bubbling buffer-saturated N$_2$ through the solution. Fractions were loaded onto 1% agarose gels containing ethidium bromide and electrophoresed for 30 min at 44 V and photographed under UV light. pSport 1 DNA was purchased from Bethesda Research Laboratories and used as received. Samples as received contained approximately 60% form I and 40% form II. Controlled potential electrolysis at 0.8 V of solutions containing DNA and Ru$^{II}$(tpy)(bpy)OH$_2^{2+}$ leads to nearly complete conversion of the supercoiled DNA to the nicked circular form in 1.5 h (lane D). Addition of Ru$^{IV}$(tpy)(bpy)O$^{2+}$ directly to the DNA effects conversion to form II in 1 h (lane H), the same amount of time required to consume all of the Ru$^{IV}$(tpy)(bpy)O$^{2+}$ under similar conditions. In control experiments, incubation of the DNA with Ru$^{II}$(tpy)(bpy)OH$_{22+}$ (lane G) or electrolysis of DNA alone for 2 h (lane F) causes no change in the supercoiled/nicked ratio.

EXAMPLE 4

Cyclic voltammetry of Ru$^{II}$(tpy) (phen)OH$_2^{2+}$

Ru$^{II}$(tpy)(phen)OH$_2^{2+}$ (phen=1,10-phenanthroline) behaves analogously to Ru$^{II}$(tpy)(bpy)OH$_2^{2+}$ during cyclic voltammetry conducted essentially as described in Example 1 above, and appears from the $i_p$-$v^{\frac{1}{2}}$ plots to bind more strongly to the DNA than Ru$^{II}$(tpy)(bpy)OH$_2^{2+}$.

EXAMPLE 5

Preparation of [Ru$^{IV}$(tpy) (Phen) O]$^{2+}$

The complex Ru(tpy)Cl$_3$ was prepared by a literature method (Leising, R. A.; Kubow, S. A.; Churchill, M. R.; Buttrey, L. A.; Ziller; J. W.; Takeuchi, K. *J. Inorg. Chem.* 1990, 29, 1306). A solution of 0.54 g of phen, 1.2 g of Ru(tpy)Cl$_3$, 0.12 g of LiCl, and 1 mL of triethylamine in 200 mL of 3:1 (v/v) EtOH/H$_2$O was refluxed for 4 hours. The solution was filtered hot and then the filtrate was placed in the refrigerator for 24 hours. A black solid [Ru(tpy)(phen)Cl]Cl (0.596 g), was collected and washed with 2×10 mL 3 M HCl, 25 mL acetone, 200 mL of ether, and air dried. This sample of [Ru(tpy)(phen)Cl]Cl was refluxed with 0.4 g of AgClCO$_4$ in 100 mL of 3:1 (v/v) acetone/H$_2$O for 1 hour. The solution was filtered to remove the resulting AgCl precipitate, and the filtrate was reduced to a volume of 20 mL. The solid [Ru(tpy)(phen)OH$_2$](ClO$_4$)$_2$ was collected and washed with cold water. Anal. Calcd.: C, 44.34; H, 2.89; N, 9.57; Found: C, 45.12; H, 3.10; N, 9.53. Oxidation with Cl$_2$ gas yields the active form, [Ru(tpy)(phen)O](ClO$_4$)$_2$ in quantitative yield.

EXAMPLE 6

Preparation of [Ru$^{IV}$(tpy)(tmen)O]$^{2+}$

A 0.190 g (0.325 mmol) sample of [Ru(tpy)(tmen)Cl](ClO$_4$) was dissolved in 20 mL of 3:1 acetone/water and 0.067 g (0.325 mmol) of AgClCO$_4$ were added. The AgCl precipitate was filtered off, and slow evaporation of the filtrate led to the precipitation of black crystals suitable for X-ray analysis of [Ru$^{II}$(tpy)(tmen)OH$_2$](ClO$_4$)$_2$ (0.12 g, 55% yield). Anal. Calcd. for C$_{21}$H$_{29}$N$_5$O$_9$RuCl$_2$: C. 37.79; H, 4.38; N. 10.49. Found: C, 37.76; H, 4.34; N, 10.40. The Ru(tpy) (tmen)O$^{2+}$ complex can be prepared quantitatively either by Che's method (C. Ho et al., *J. Chem. Soc.*, Dalton Trans. 1990, 967) or by oxidation of [Ru$^{II}$(tpy)(tmen)OH$_2$]ClO$_4$)$_2$ in aqueous solution with Cl$_2$ gas.

EXAMPLE 7

Preparation of [Ru$^{IV}$(phen)$_2$(py)O}$^{2+}$

The preparations are directly analogous to the bpy complexes. Ru(phen)$_2$Cl$_2$·3H$_2$O was prepared by the method of Sullivan et al. (Sullivan, B. P.; Salmon, D. J.; Meyer, T. J. *Inorg. Chem.* 1976, 17, 3334). Ru(phen)$_2$(NO$_2$)$_2$·H$_2$O was prepared from this complex by the method of Godwin and Meyer ( Godwin, J. B.; Meyer, T. J. *Inorg. Chem.* 1971, 10, 471). Ru(phen)$_2$(py)(NO)](PF$_6$)$_3$ was prepared from this complex by the method of Callahan and Meyer (Callahan, R. W.; Meyer, T. J., *Inorg. Chem.* 1977, 16, 574). The nitrosyl complex was converted in 86% yield to the aqua complex, [Ru(phen)$_2$(py)OH$_2$(PF$_6$)$_2$·2H$_2$O, by the method of Moyer and Meyer (*J. Inorg. Chem.* 1981, 20, 436). Anal. Calcd: C, 39.43; H, 3.04; N, 7.91; Found: C, 39.44; H, 3.10, N, 8.09. Oxidation with Cl$_2$ gas or Ce(IV) yields the active form of the complex in quantitative yield.

EXAMPLE 8

Preparation of Ru$^{IV}$(tpy)(tmen-AO)O$^{2+}$

Ru(tpy)(tmen-AO)O$^{2+}$ (AO means Acradine Orange) is synthesized as follows:

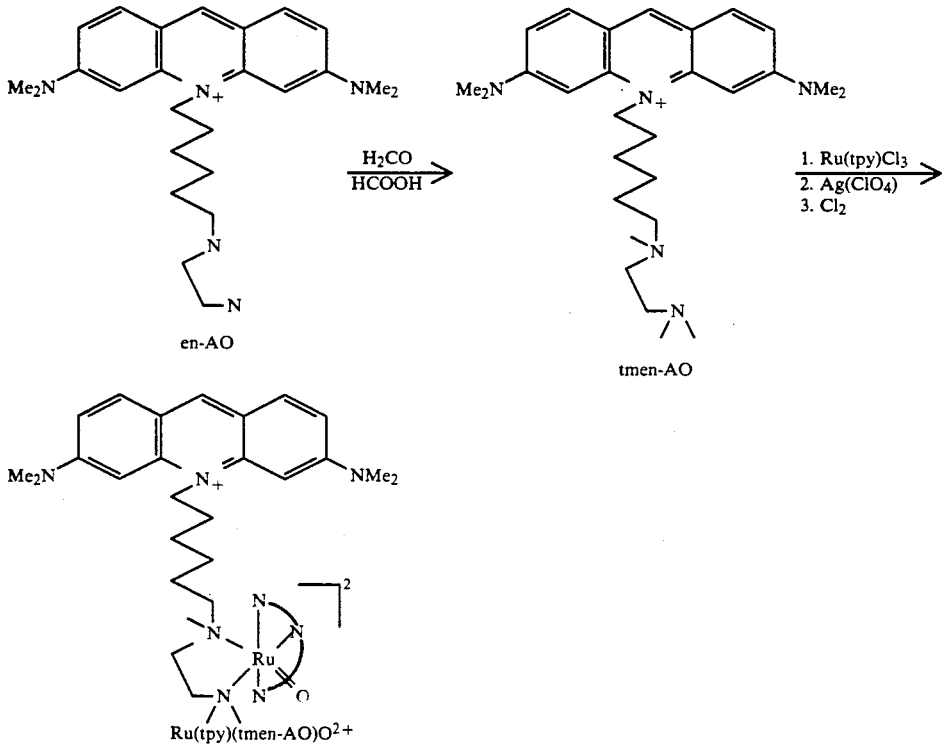

The starting ligand en-AO is prepared by the method of Bowler, B. E.; Ahmed, K. J.; Sundquist, W. I.; Hollis L. S.; Whang, E. E.; Lippard, S. J. *J. Am. Chem. Soc.* 1989, 111, 1299. The remaining steps are conducted in accordance with techniques which will be apparent to those skilled in the art in light of existing syntheses.

The foregoing examples are illustrative of the present invention, and are not to be construed as limiting thereof. The invention is defined by the following claims, with equivalents of the claims to be included therein.

That which is claimed is:

1. A process of cleaving deoxyribo nucleic acids, comprising contacting deoxyribo nucleic acids with an oxoruthenium(IV) coordination complex of the formula L-Ru$^{IV}$O$^{2+}$, wherein L is selected from the group consisting of inert polypyridyl ligands and inert polypyridyl ligands sets, and wherein L contains five nitrogen atoms bonded to Ru$^{IV}$ by coordination bonds so that said coordination complex has an octahedral orientation, the coordination complex provided in an amount effective to cleave the nucleic acid.

2. A process according to claim 1, wherein L is a ligand set, the members of said ligand set are selected from the group consisting of pyridien, 2,2'-bipyridine, 2,2',2"-terpyridine, 1,10-phenanthroline,N,N'-tetramethylenediamine.

3. A process of cleaving deoxyribo nucleic acids, comprising contacting deoxyribo nucleic acids with an oxoruthenium(IV) coordination complex selected from the group consisting of Ru$^{IV}$(tpy)(bpy)O$^{2+}$, Ru$^{IV}$(tpy)(phen)O$^{2+}$, RU$^{IV}$(tpy)(tmen)O$^{2+}$, RU$^{IV}$(bpy)$_2$(py)$^{2+}$, Ru$^{IV}$(phen)$_2$(py)$^{2+}$, and RU$^{IV}$(tpy)(tmen-AO)O$^{2+}$, the coordination complex provided in an amount effective to cleave the nucleic acid.

4. A process of cleaving deoxyribo nucleic acids, comprising contacting a deoxyribo nucleic acid with the oxoruthenium(IV) coordination complex of Formula (I) below:

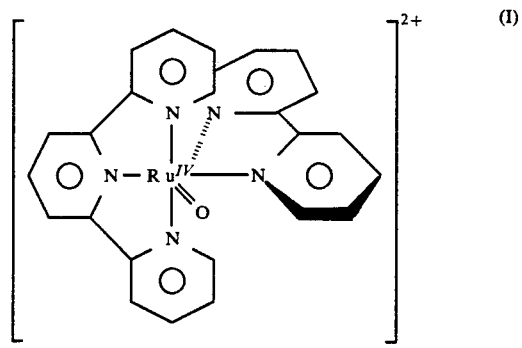

the coordination complex provided in an amount effective to cleave the nucleic acid.

* * * * *